United States Patent [19]

Baxter et al.

[11] 4,217,180
[45] Aug. 12, 1980

[54] METHOD OF DETERMINING SUSCEPTIBILITY OF ALLOYS TO STRESS CORROSION CRACKING

[75] Inventors: William J. Baxter, Bloomfield Hills, Mich.; David R. Arnott, North Rockhampton, Australia

[73] Assignee: General Motors Corporation, Detroit, Mich.

[21] Appl. No.: 58,138

[22] Filed: Jul. 17, 1979

[51] Int. Cl.² .................. G01N 27/42; G01N 3/08
[52] U.S. Cl. ........................... 204/1 T; 204/58; 204/195 R
[58] Field of Search ............... 204/1 T, 58, 195 R

[56] References Cited

U.S. PATENT DOCUMENTS

| | | | |
|---|---|---|---|
| 3,408,270 | 10/1968 | Gentile | 204/1 T |
| 3,419,479 | 12/1968 | Klein | 204/1 T |
| 3,437,568 | 4/1969 | Hasselmann et al. | 204/1 T X |
| 3,710,616 | 1/1973 | Smith et al. | 204/1 T X |
| 4,019,129 | 4/1977 | Grau | 204/1 T X |

*Primary Examiner*—Arthur C. Prescott
*Attorney, Agent, or Firm*—Lawrence B. Plant

[57] ABSTRACT

Accelerated testing method for determining the susceptibility of alloys to stress corrosion cracking. Test parts are anodized to form an oxide coating thereon. The anodized parts are deformed to a known amount of tensile strain sufficient to rupture the oxide. Microcracks created in the oxide coating occur at the situs of where stress corrosion cracks will occur in service. The parts are reanodized such as to anodically heal the microcracks and the reanodization current transient recorded. The rate of current decay during reanodization is indicative of the alloy's susceptibility to stress corrosion cracking.

1 Claim, 3 Drawing Figures

METHOD OF DETERMINING SUSCEPTIBILITY OF ALLOYS TO STRESS CORROSION CRACKING

BACKGROUND OF THE INVENTION

This invention relates to testing alloys to determine their susceptibility to stress corrosion cracking.

Many alloys are known to fail prematurely under the combined influence of tensile stress and corrosive environments, due to the formation and growth of cracks of an almost brittle nature. This phenomenon, whereby the load bearing capability of an alloy is decreased by a corrosive service environment, is known as stress corrosion cracking (hereafter S.C.C.). Though not completely understood the S.C.C. phenomenon is described more fully in Shrier, L. L., *Corrosion*, J. Wiley and Sons, New York (1963 ). S.C.C. occurs under a wide variety of circumstances, and is dependent upon specific combinations of the corrosive environment and the composition and microstructure of the alloy. Quality control test procedures are required to assess the susceptibility of an alloy to S.C.C. prior to fabrication of components.

Various test procedures have been devised [see Parkins et al., Br. Corros. J. 7, 154 (1972)], consisting primarily of either so-called constant load or constant total strain tests, often conducted under conditions of alternate exposure to the corrosive solution and to air. Unfortunately, the duration of such tests is typically about 30–90 days. There are at present several approaches to reducing the test duration, for example, by applying an electric potential to the sample, or by using boiling corrosive liquids. In recent years the constant rate test has been slowly gaining in popularity for investigative purposes, and appears to be the most rapid test at the present time. However, even this procedure requires a minimum of about one day.

It is an object of this invention to provide still faster yet reliable test for determining the susceptibility of an alloy to S.C.C. It is a further object of this invention to provide a test which relies upon measuring the rate of oxidation of the elements in a previously oxidized alloy which are revealed to an electrochemical environment following the application of an external load thereto.

The invention may better be appreciated in the light of certain earlier proposed theories for S.C.C. According to these theories the surface of corrosion resistant metals is covered by an inert film, usually an oxide, which protects the electrochemically active metal from the corrosive environment. If this protective film is ruptured, as occurs during plastic deformation of the metal, the exposed metal surface is attacked or even dissolved by the corrosive environment, until a new protective or "passivating" film can reform. As plastic deformation is continued this fresh film will in turn be ruptured and the metal dissolution and repassivation process repeated, thereby generating an active path for a stress corrosion crack. The details of this mechanism have not been completely resolved, particularly with regard to the nature of the material revealed when the oxide film is ruptured and the subsequent electrochemical reactions. However, since pure metals are not susceptible to S.C.C. it seems clear that the alloying elements play a role in the S.C.C. mechanism. In some systems, for example, aluminum alloys, the path of the stress corrosion crack, which is intergranular, is preordained by the distribution of the alloying elements in the microstructure. These elements are present in the grains as strengthening precipitates, but there is preferential precipitation in the grain boundaries so that a very narrow and softer precipitate-free zone (PFZ) develops immediately adjacent to the boundaries. Plastic deformation tends to be concentrated in the PFZ.

BRIEF DESCRIPTION OF THE INVENTION

Our photoelectron microscopic investigation has shown that 7075 aluminum, for example, is not only susceptible to S.C.C., but rupture of the oxide film thereon is confined to the PFZ. With this in mind, we simulate the film rupture mechanism in a well controlled manner, much the same as was done in copending U.S. patent application Baxter U.S. Ser. No. 898,614 (filed Apr. 21, 1978) now U.S. Pat. No. 4,160,702 for early assessment of metal fatigue. We then plastically deform the material sufficiently to rupture or crack the oxide film, and measure the rate of electrochemical reoxidation of the alloy revealed at the cracks. The rate of the reoxidation is shown to be a function of both the total amount and the nature of the alloying elements exposed.

The invention will better be understood with reference to certain test results which are described hereafter in conjunction with the Figures.

THE INVENTION

Figure 1:
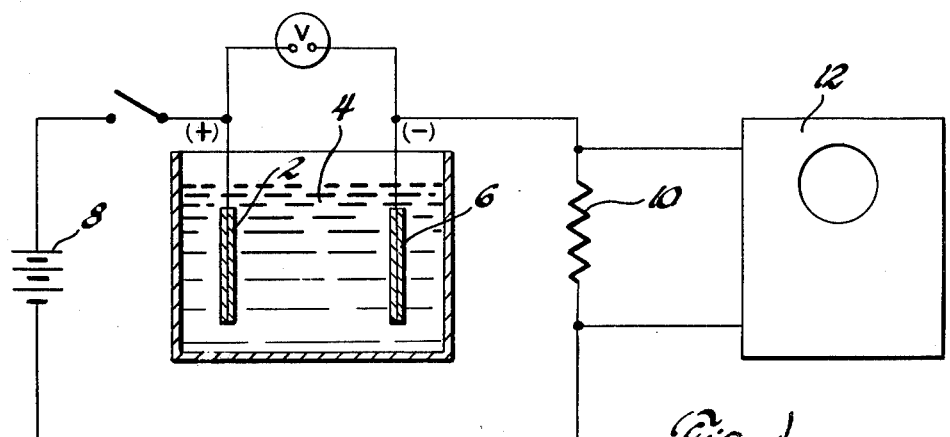
FIG. 1 depicts the test apparatus for determining the electrochemical current transients of the present invention.

The invention contemplates: anodizing the surface of the alloy to be tested at an arbitrarily selected predetermined voltage to build up a current-limiting oxide coating on the part which causes the anodizing current to decline with time to an arbitrarily selected cut-off level which determines the thickness of the oxide; deforming the part dry (in air) to produce a known amount of tensile strain sufficient to rupture and microcrack the oxide layer and thereby reveal the underlying metal; reanodizing the part at slightly less than the anodizing voltage to insure that only the cracks see the anodizing current and allowing the reanodizing current to decline to a selected cut-off current which is a fraction of the initial reanodization current; recording the total current transient on the part during reanodization and therefrom calculating the current decay rate during reanodization; and comparing the decay rate (i.e., per unit area of sample) to the unit area decay rates of other alloys and known standards. The unit area decay rate is sensitive to the identity of the material being reoxidized and is indicative of the susceptibility of the particular alloy to S.C.C.

In order to evaluate the results obtained during reanodization, it is necessary to know how (i.e., voltage-current) the original oxide coating was formed. In this regard, during the anodizing process there is an initially high flow of current when the bare alloy is directly in contact with the electrolyte, but the anodizing current rapidly declines to a significantly lower level as the highly resistive oxide coating builds up and passivates the alloy. The precise nature of the oxide coating will depend on the alloy being anodized, the electrolyte employed, the anodizing potential (i.e., voltage) and the cut-off current selected. The particular combination of anodizing conditions is not particularly important—rather only that they be known and substantially reproducible during the reanodization step.

Following anodization, a known amount of tensile strain is (i.e., deformation) applied to the alloy, as, for example, in an Instron machine. Following deformation, the alloy is reanodized under substantially the same conditions as the initial anodization. In this regard, the reanodization voltage should be no more than the anodization voltage or else the overall coating thickness would increase and tend to mask the significance of the current transients as they relate to the microcracks. Preferably, the reanodization voltage is slightly less than the anodization voltage to insure that all the current transients result from microcrack healing. During reanodization, the current drops from an initial reanodization current ($I_o$) to an appropriate cut-off current. Typically, the cut-off current is the initial current ($I_o$) divided by e (i.e., 2.718), though other cut-off current values could be used so long as they permit a fair calculation of the current decay rate. The current transient is recorded and a time constant (i.e., $\tau/A$) calculated. The time constant is the time required for the reanodization current to decay from the initial value ($I_o$) to the cut-off value per unit area of sample tested. The time constants, so determined, are indicative of the relative susceptibility of the alloys to S.C.C.

Initial anodization and reanodization is performed in apparatus such as shown in FIG. 1 in order that the anodization and reanodization conditions can be accurately determined and duplicated. The test specimen 2 is immersed and anodically polarized in an electrolyte 4 appropriate to the composition of the specimen 2. A cathodically polarized counterelectrode 6 is positioned opposite the specimen 2 in the electrolyte 4. Appropriate means (e.g., battery, rectifier,. etc.) 8 are provided to impress anodizing and reanodizing potential/current on the electrodes. A resistor 10 is connected in series with the means 8 and electrodes 2-6 and a recording, digital storage oscilloscope 12 is used to record the current transients such as illustrated in FIG. 2.

For example, the specimens are anodized in a 3% by weight tartaric acid electrolyte (i.e., acid adjusted to a pH of 5 with ammonium hydroxide) using another piece of aluminum as the cathode. At the beginning of the anodization and before any significant oxide had formed, the applied voltage is gradually increased to the desired voltage so as to keep the anodization current density below about 10 milliamperes per square centimeter ($ma/cm^2$). When the desired anodization voltage (e.g., about 20 volts) is achieved, the voltage is held constant but the current allowed to decline from an initial 10 $ma/cm^2$ rate to an arbitrarily selected cut-off level of about $1 \times 10^{-3}$ $ma/cm^2$. At the end of about twenty minutes an oxide coating of about twenty-eight nanometers is produced on the surface of the specimen.

The specimens are then tensile strained in an Instron machine, to a predetermined level sufficient to rupture the oxide film. The gage sections of the samples are then reanodized but at a slightly lower voltage than the initial anodization voltage, and the current transient recorded.

Figure 2:
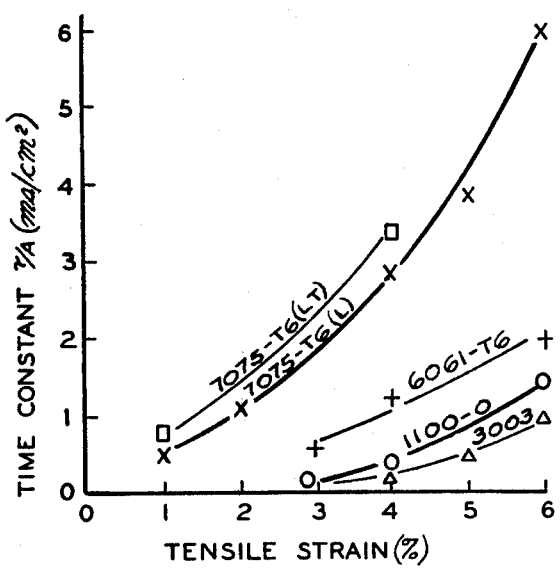
FIG. 2 illustrates the effect of tensile strain on the reanodization time constant for several Al alloys.

FIG. 2 is a plot of the results obtained in one specific feasibility test of the invention and is a plot of the time constant obtained during reanodization v. the amount of tensile strain applied to the particular aluminum specimens under investigation. The several specimens were strained to different levels by known amounts as determined by the movement of an Instron machine's crosshead which had been earlier calibrated with an extensometer using identical specimens.

The rate of reoxidation is characterized here by the rate of decay of the reanodization current transient, which is expressed as the time constant of the decay during reanodization of a unit area of the specimen ($\tau/A$ in $msec/cm^2$). This time constant is shown in FIG. 2 as a function of the tensile strain for a series of aluminum alloys with quite different susceptibilities to S.C.C. The 1100, 3003 and 6061-T6 alloys are not susceptible to S.C.C. and have small time constants for reanodization. The 7075-T6 alloy is susceptible to S.C.C. and has much larger values of the time constant.

For all these materials, the time constant increases with tensile strain because of the increasing extent of rupture of the oxide. The important feature here, however, is that for a fixed amount of tensile strain there is a distinct difference in the time constant for each alloy. This difference between alloys is not related to differences between the extent or area of the microcracks in the oxide. In fact, quite the reverse is true. For example, photoelectron microscopy studies have shown that the density of microcracks in the oxide on 1100 aluminum is at least an order of magnitude greater than that on 7075-T6 aluminum. Thus, the difference between the curves in FIG. 2 arises because the material revealed is quite different in each alloy system and reoxidizes at a different rate. In particular, in the case of the 7075-T6 alloy, the reoxidation rate is considered to be controlled by the precipitates of the alloying elements Mg, Zn, etc. which are more concentrated in the grain boundary regions where the oxide rupture occurs.

Figure 3:
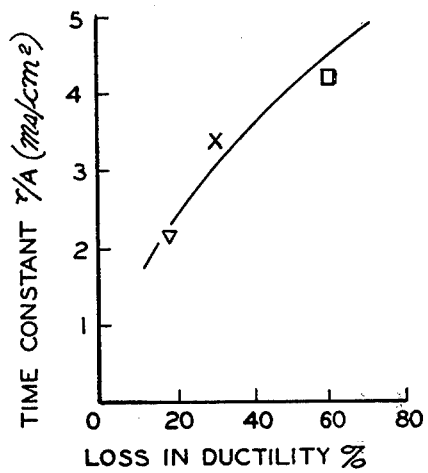
FIG. 3 illustrates the relationship between the reanodization time constant for 7075 aluminum and the loss in ductility due to stress corosion cracking.

The two curves for the 7075-T6 alloy shown in FIG. 2 are for samples with different orientations to the rolling direction of the sheet. It is well known that when the tensile strain is parallel to the rolling direction (designated as L) the susceptibility to S.C.C. is lower than when the tensile strain is perpendicular to the rolling direction (designated as LT). The time constants produced here are consistent with that known relationship as to S.C.C. susceptibility. Finally, the 7075-T6 (LT) alloy was heat treated by well known procedures to produce three states of susceptibility to S.C.C. The susceptibility to S.C.C. in a solution of $AlCl_3$ was measured by the constant strain rate technique (at a strain rate of $9 \times 10^{-7}$ $sec^{-1}$), and is expressed in FIG. 3 as the loss in ductility (total elongation) relative to that attainable when deformed under normal atmospheric conditions. The values of the reanodization time constant for identically heat treated material was measured after a tensile strain of $4 \times 10^{-2}$. The correlation between the time constant and the susceptibility to S.C.C. is illustrated in FIG. 3.

While this invention has been exemplified primarily in terms of aluminum, it is likewise applicable to other metals susceptible to controllable anodic oxidation as is well known in the art (e.g., L. Young, *Anodic Oxide Films,* Academic Press, (1961). Hence, this invention is not intended to be limited except to the extent set forth hereafter in the claims which follow.

The embodiments of the invention in which an exclusive property or privilege is claimed are defined as follows:

1. A testing method for determining the susceptibility of alloys to stress corrosion cracking comprising the steps of:

anodizing the surfaces of samples of said alloys at a predetermined potential in an appropriate electrolyte to form current-limiting oxide coatings thereon;

straining the samples to a predetermined level sufficient to induce the formation of microcracks in said coatings;

reanodizing said samples in said electrolyte at a potential of about said predetermined anodizing potential or less until the reanodization current decays from an initial value to a predetermined fraction of said initial value;

determining the times required to perform said reanodizations; and comparing the reanodization time per unit area of each sample with the reanodization times per unit area of the other samples as an indicator of the relative susceptibility of the samples to stress corrosion cracking.

* * * * *

UNITED STATES PATENT AND TRADEMARK OFFICE
CERTIFICATE OF CORRECTION

PATENT NO. : 4,217,180
DATED : August 12, 1980
INVENTOR(S) : William J. Baxter, David R. Arnott It is certified that error appears in the above-identified patent and that said Letters Patent are hereby corrected as shown below:

Column 1, line 32, after "constant" insert -- strain --.

Signed and Sealed this

Third Day of February 1981

[SEAL]

Attest:

RENE D. TEGTMEYER

Attesting Officer

Acting Commissioner of Patents and Trademarks